United States Patent [19]
Dance et al.

[11] Patent Number: 5,520,694
[45] Date of Patent: May 28, 1996

[54] APPARATUS AND METHOD FOR ALIGNING KNEE PROSTHESES

[76] Inventors: Mark N. Dance, 4977 556 St., Ladner, B.C., Canada, V4K 3C2; Gordon C. Sims, 2632 SE. Grant St., Portland, Oreg. 97214; Geoffrey F. Auchinleck, 302 - 1233 Beach Ave., Vancouver, B.C., Canada, V6E 1V4

[21] Appl. No.: 369,140

[22] Filed: Jan. 5, 1995

Related U.S. Application Data

[63] Continuation of Ser. No. 80,950, Jun. 21, 1993, abandoned.

[51] Int. Cl.$^6$ .............................. A61F 5/00; A61B 17/58
[52] U.S. Cl. .................. 606/86; 606/87; 606/88; 606/102
[58] Field of Search .................. 606/79, 80, 86, 606/87, 88, 96, 97, 98, 102

[56] References Cited

U.S. PATENT DOCUMENTS

| | | |
|---|---|---|
| 4,467,801 | 8/1984 | Whiteside . |
| 4,474,177 | 10/1984 | Whiteside . |
| 4,524,766 | 6/1985 | Petersen . |
| 4,558,697 | 12/1985 | Wu ............................... 606/86 |
| 4,571,834 | 2/1986 | Fraser et al. . |
| 4,574,794 | 3/1986 | Cooke . |
| 4,739,751 | 4/1988 | Sapega . |
| 4,773,407 | 9/1988 | Petersen . |
| 4,935,023 | 6/1990 | Whiteside et al. . |
| 4,938,762 | 7/1990 | Wehrli . |
| 4,950,271 | 8/1990 | Lewis . |
| 4,969,895 | 11/1990 | McLeod . |
| 5,002,545 | 3/1991 | Whiteside et al. . |
| 5,007,912 | 4/1991 | Albrektsson et al. . |
| 5,071,420 | 12/1991 | Paulos . |
| 5,122,145 | 6/1992 | Fishbane . |
| 5,141,512 | 8/1992 | Farmer . |
| 5,154,717 | 10/1992 | Matsen, III et al. . |
| 5,289,826 | 3/1994 | Kovacevic ............................... 606/102 |
| 5,364,401 | 11/1994 | Ferrante ................................... 606/102 |
| 5,385,567 | 1/1995 | Goble ........................................ 606/86 |
| 5,409,489 | 4/1995 | Sioufi ....................................... 606/86 |
| 5,411,503 | 5/1995 | Hollstien ................................. 606/86 |

FOREIGN PATENT DOCUMENTS

| | | |
|---|---|---|
| 0322363 | 6/1989 | European Pat. Off. . |
| 0326768A2 | 8/1989 | European Pat. Off. . |
| 0446659 | 1/1992 | European Pat. Off. . |
| 2587198 | 3/1987 | France . |
| 8807840 | 10/1988 | WIPO . |

*Primary Examiner*—Michael A. Brown
*Attorney, Agent, or Firm*—Klarquist, Sparkman, Campbell, Leigh & Whinston

[57] ABSTRACT

An apparatus for aligning a surgical instrument having a connection device attached to the femur in the vicinity of the knee joint at a point chosen to be on the mechanical axis. An adjustable vertical suspension device attached to the femur for counteracting the moment about the hip joint created by the weight of the femur. A vertical tension indicating device attached to the adjustable vertical suspension device.

4 Claims, 2 Drawing Sheets

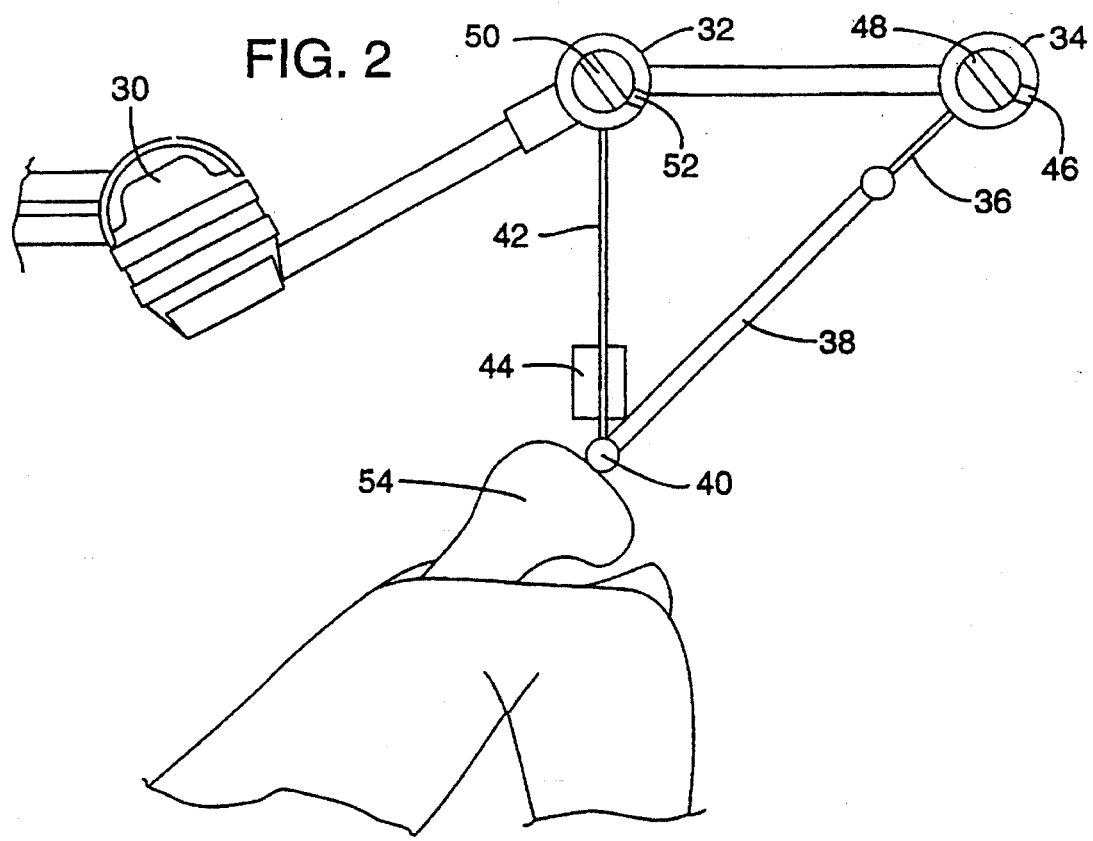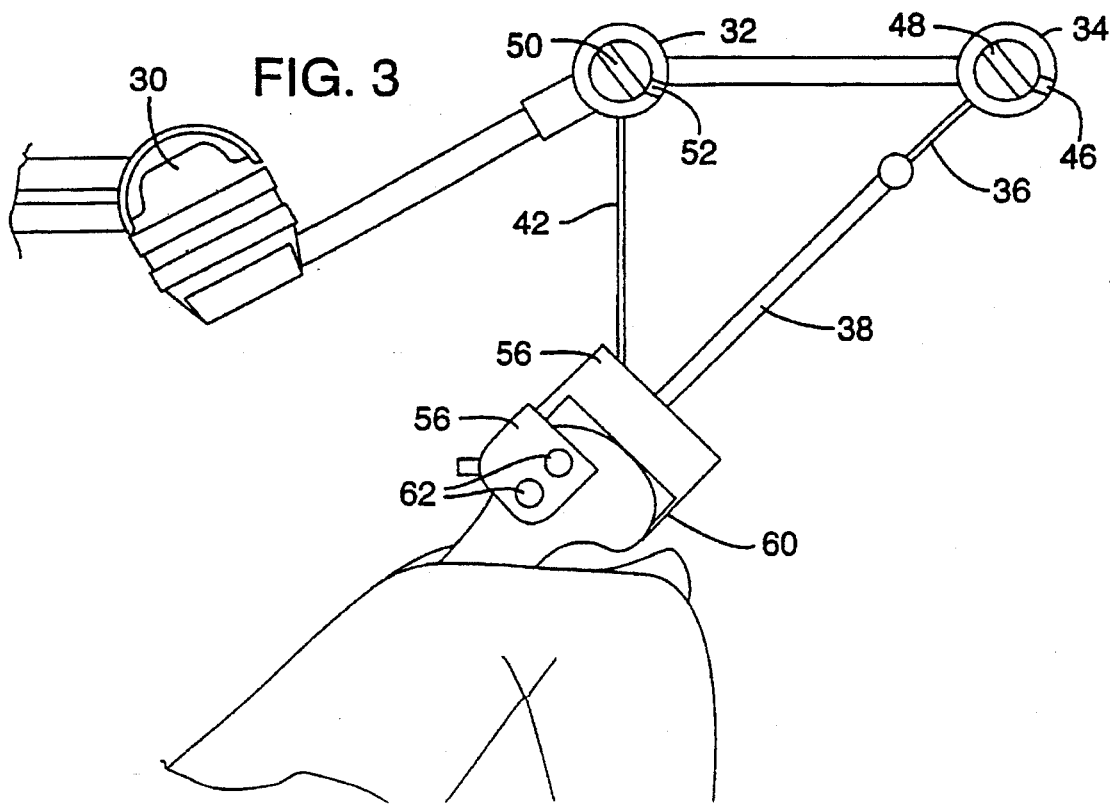

APPARATUS AND METHOD FOR ALIGNING KNEE PROSTHESES

This is a continuation of U.S. patent application Ser. No. 8/080,950, filed Jun. 21, 1993, now abandoned.

FIELD OF THE INVENTION

The present invention refers to a method and apparatus for establishing the correct alignment end orientation required for a knee prosthesis during total knee arthroplasty surgery. In particular, the invention pertains to determining the correct position and orientation of cutting guides with respect to patient's femur or tibia so that the femur or tibia can be cut to fit the knee prosthesis such that the prosthesis will be implanted in anatomically correct orientation,

BACKGROUND OF THE INVENTION

During knee resurfacing arthroplasty, commonly called knee replacement surgery, the distal surfaces of the femur are cut away and replaced with an metal cap to simulate the baring surfaces of the femur. The proximal surface of the tibia is modified in a similar way, to provide a metal-backed plastic bearing surface. The metal femoral component of the new "artificial joint" transfers the patient's weight to the tibial component such that the joint can support the patient's weight and provide a near-normal motion of the knee joint.

Several studies have indicated that the long term survival of such an artificial knee joint is dependant on how accurately the components of the knee joint are implanted with respect to the weight bearing axis of the patient's leg. In a correctly functioning knee, the weight bearing axis passes through the centre of the head of the femur, the centre of the knee and the centre of the ankle joint. This weight bearing axis is typically located by analyzing an X-ray image of the patient's leg, taken while the patient is standing.

The X-ray image is used to locate the centre of the head of the femur and to calculate its position relative to selected landmarks on the femur. The selected landmarks were then found on the patient's femur during surgery and the calculations used to estimate the actual position of the femoral head. These two pieces of information are used to determine the correct alignment of the weight bearing axis for the femur. To completely define the correct position for the femoral component of the knee prosthesis, the correct distance between the centre of the femoral head and the knee joint and the rotation of the knee joint about the weight bearing axis must be established. These two pieces of information are determined from landmarks on the distal portion of the femur. The correct alignment for the tibial component of the knee prosthesis is determined by finding the centre of the ankle joint and relating its position to landmarks on the tibia. This point and the centre of the proximal tibial plateau are used to define the weight bearing axis of the tibia. The correct distance between the ankle joint and the knee joint and the rotation of the knee joint about the weight bearing axle are determined by reference to the distal portion of the femur and landmarks on the tibial plateau.

Various mechanical alignment instruments am used to assist the surgeon in making cuts on the distal femur and proximal tibia which will allow the femoral and tibial components of the new knee joint to be attached to the femur and tibia. These mechanical alignment instruments permit the surgeon to fix cutting guides in place with respect to the selected landmarks on the bones so that the cuts will be correctly oriented with respect to the weight bearing axis determined from the X-ray image.

There are two general types of alignment instruments in common use. These are intramedullary and extramedullary alignment systems. Intramedullary alignment systems use the inside of the femur or tibia, the medullary canal, as one of the selected landmarks for establishing alignment. Extramedullary alignment systems use only the external surfaces of the body to establish alignment.

A typical extramedullary alignment system requires the surgeon to visually align a slender rod with the centre of the knee and the centre of the femoral head for alignment of the femoral component, then align a similar rod with the centre of the ankle and the centre of the tibial plateau for alignment of the tibial component. The centers of the femoral head and ankle are found by either palpitation or established with an intraoperative X-ray. If correctly placed, the rods will lie parallel to, and offset from the weight bearing axis. Once aligned, the rods are used as a guide to fix the location of the cutting guides with respect to the femur and tibia so that the cuts can be performed.

A typical intramedullary alignment system requires the surgeon to insert a rod into the medullary canal of the femur and tibia. If properly placed, these rods should lie on the axis of the bones. In the case of the tibia, the weight bearing axis is very close to the axis of the bone. In the case of the femur the axis of the bone is quite different from the weight bearing axis due to the offset nature of the hip joint, and this difference must be measured from the pre-operative X-ray and used to correct the alignment of the femoral cutting jigs.

Both intramedullary and extramedullary approaches to alignment have numerous inherent drawbacks and sources of error. Extramedullary alignment depends on accurate visual estimation of the alignment of the extramedullary rods. Location of the femoral head by palpitation is difficult and error prone, particularly with obese patients. Use of intraoperative X-rays improves the result somewhat, but this is time consuming and exposes the patient and operating room personnel to radiation. X-rays are also subject to distortion and require visual interpretation and estimation to correctly analyze, as they offer only one planar view in two dimensions.

Intramedullary alignment approaches provide only slightly better results, in that the knee joint alignment is still determined by estimating the difference between the bone axis and the weight bearing axis from a potentially distorted X-ray image. In addition, intramedullary rods must be introduced very carefully, not only to make sure they align correctly with the medullary canal, but also to make sure that the insertion of the rods does not create an embolism, which could kill or seriously injure the patient.

An ideal alignment system finds the weight bearing axis of the patient's leg directly, without the need for preoperative or intraoperative X-rays, estimation, calculation, location of hidden or obscured landmarks, or surgical intervention outside of that required for access to the knee joint surfaces. The ideal alignment system depends only on the accepted definition that the weight bearing axis passes through the centre of the head of the femur, the centre of the knee joint and the centre of the ankle, in order to locate the weight bearing axis.

SUMMARY OF THE INVENTION

The present invention provides apparatus and method for locating the weight bearing axis of a patient's limb by directly locating the centers of rotation of the head of the femur and ankle. These centers of rotation are combined with easily identified landmarks on the distal femur and proximal tibia to simply and accurately define the actual weight bearing axis of the patient's limb.

In one aspect, the invention provides apparatus for: connecting a tension member to a selected point on the distal femur; applying a force to counter balance any moment about the hip joint which results from the weight of the femur and tibia; applying tension to the tension member to pull the mechanical axis of the femur into alignment with the tension member; and attaching one or more cutting guides to the tension member to align them with the mechanical axis of the femur. The invention also provides a method for finding the mechanical axis of the femur, including the steps of: providing an attachment point on the distal femur at the centre of the knee joint; balancing the moment about the hip joint which results from the weight of the femur and tibia; applying tension to the attachment point; allowing the femur to move freely so that the mechanical axis of the femur is aligned with the axis of the applied tension; and using the axis of the applied tension to indicate the mechanical axis of the femur.

BRIEF DESCRIPTION OF THE DRAWINGS

FIG. 2 is a pictorial view of a tension alignment system in accordance with the invention.

FIG. 3 shows the alignment system of FIG. 2 with the carriage and bone clamp attached.

DESCRIPTION OF THE PREFERRED EMBODIMENT

Figure 1A:
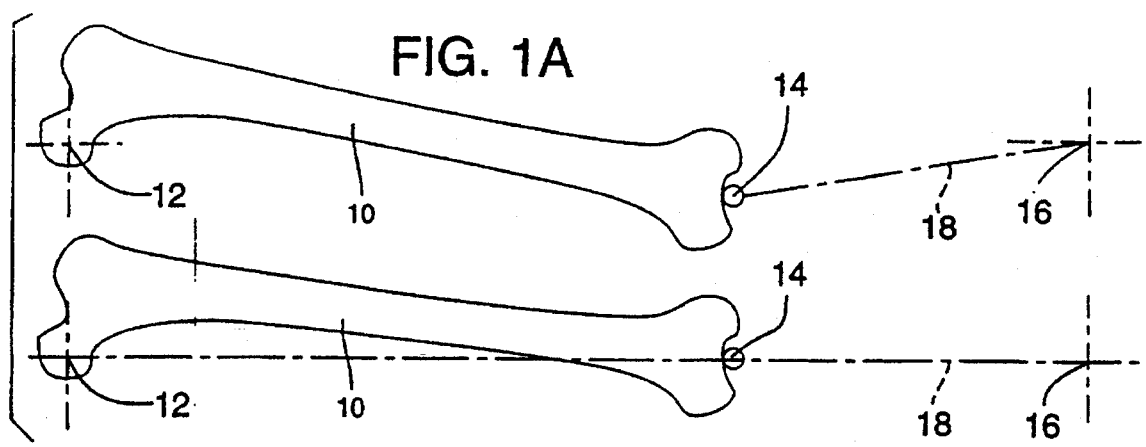
FIGS. 1a–1b are schematic representation of the tension alignment system.

FIG. 1a shows in schematic form how the tension alignment system operates, as viewed in the coronal plane, assuming that the patient is supine. Femur 10 is constrained to rotate about the centre of femoral head 12. Attachment point 14 is chosen to be at the centre of the knee joint. Attachment point 14 will typically be located approximately 1 cm anterior to the femoral attachment of the posterior cruciate ligament. Tension member 18 is connected between attachment point 14 and fixed point 16. Tension member 18 may be of a flexible material capable of applying only tension, or alternatively may be attached to attachment points 14 and 16 such that the attachments are free to rotate and no moments are supported by either attachment point. To establish the alignment axis, tension is applied to tension member 18. Femur 10 will rotate about femoral head 12 until the axis of tension member 18 passes through the centre of femoral head 12.

Figure 1B:
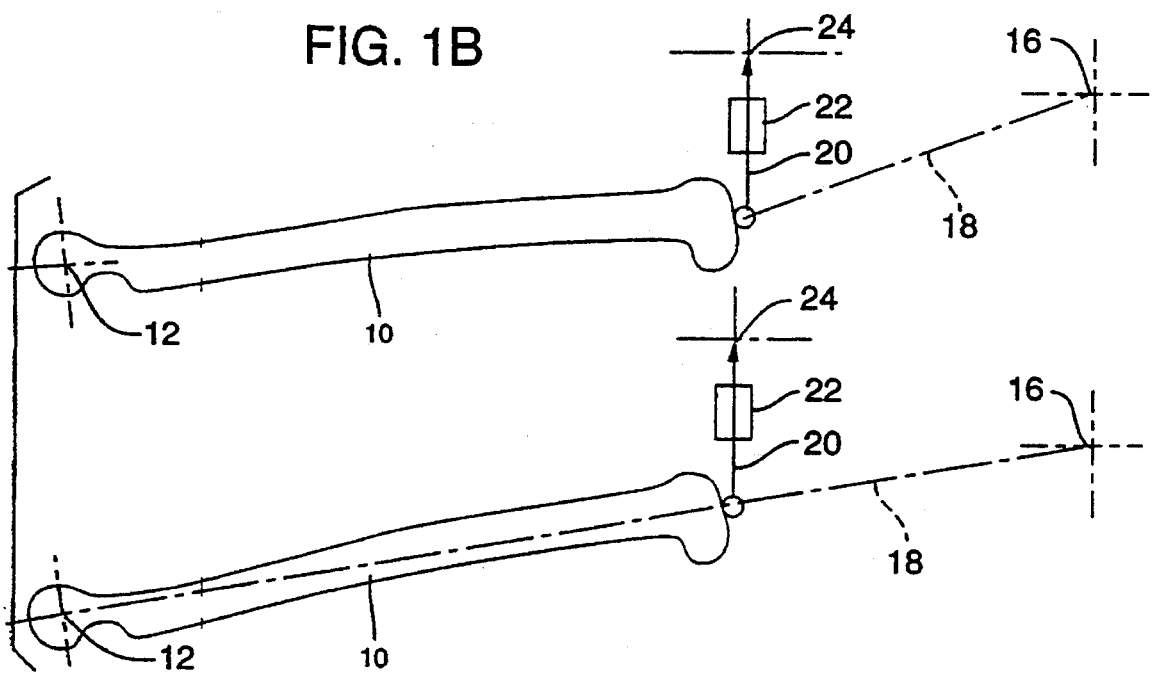

FIG. 1b shows in schematic form how the tension alignment method operates as viewed from the sagital plane, assuming that the patient is supine. Attached at or near attachment point 14 is weight support line 20. Weight support line 20 is attached to tension indicating device 22, which may be a spring type scale. Tension indicating device 22 is connected to fixed point 24, which is chosen to lie directly above attachment point 14. To establish the alignment axis, the tension required to counteract the moment about the hip joint due to the weight of femur 10 is recorded from tension indicating device 24. Tension is applied to tension member 18. Weight support line 20 is then tightened until tension indicating device 24 indicates the same force as originally recorded. In this way, the moment about the hip joint due to the weight of femur 10 is removed from tension member 18 so that tension member 18 will not be deflected by the weight of femur 10. When the deflection is eliminated, the axis of tension member 18 passes through the centre of femoral head 12.

FIG. 2 shows one possible embodiment of an apparatus which aligns a cutting guide to the mechanical axis of the femur. Connection point 40 is a ball end fitting attached to a threaded post. The threaded post is screwed into the end of femur 54 at a point chosen to be at the mechanical centre of the knee joint, usually located approximately 1 cm anterior to the femoral attachment of the posterior cruciate ligament. Attached to connection point 40 is alignment rod 38, which is attached so that it can freely rotate about connection point 40. The distal end of alignment rod 38 is attached to tension cable 36. Tension cable 36 is connected to tension reel 34 such that tension cable 36 can be wound on to tension reel 34 with crank 48 to increase the tension in tension cable 36. Tension reel 34 includes a ratchet mechanism to stop tension cable 36 from unreeling from the tension reel once tension is applied. Ratchet release 46 allows a user to release the ratchet and unreal tension cable 36 when desired.

Also connected to connection point 40 is tension indicator 44, which in the preferred embodiment is a spring scale with an indicating pointer calibrated to measure tension in pounds and kilograms. Attached to the distal end of tension indicator 44 is support cable 42. Support cable 42 is connected to tension reel 32 such that support cable 36 can be wound on to tension reel 32 with crank 50 to increase the tension in support cable 42. Tension reel 32 includes a ratchet mechanism to stop support cable 42 from unreeling from the tension reel once tension is applied. Ratchet release 52 allows a user to release the ratchet and unreal support cable 42 when desired.

The alignment system is connected to support arm 30 so that it may be suspended generally above femur 54. Any fixed support located generally above femur 54 capable of supporting the weight of femur 54 and the alignment system would be suitable. In the preferred embodiment, the support arm is an Endex Endoscopy Positioning System (Andronic Devices Ltd., Richmond, B.C. Canada) in use, connection point 40 is first screwed into the distal femur at the point where the mechanical axis of the femur passes through the knee joint. Support arm 30 is moved into position above femur 54 so that tension reel 32 is located directly over femur 54 and support cable 42 hangs vertically over connection point 40. Tension indicator 44 is connected to connection point 40. Excess length of support cable 42 is reeled onto tension reel 32 until the weight of femur 54 is fully supported. The tension indicated by tension indicator 44 is then recorded. Tension rod 38 is then connected to connection point 40. Excess length of tension cable 36 is reeled onto tension reel 34 until a tension of more than approximately 20 pounds is reached. Tension reel 32 is then re-adjusted until the tension indicated on tension indicator 44 is equal to the previously recorded value. At this point, alignment rod 38 is aligned with the mechanical axis of femur 54 in all planes.

Referring to FIG. 3, carriage 56 is placed over tension rod 38 and moved along tension rod 38 until the proximal face of carriage 56 is in contact with the distal face of femur 54 to establish a reference distance between the femoral head and the knee joint. Alignment skid 60 of carriage 56 is brought into contact with the posterior face of the condyles of the femur to establish rotational alignment of the distal femur about the mechanical axis.

Attached to carriage 56 is bone clamp 58. Bone clamp 58 is attached to femur 54 in the position determined by carriage 56 using screws 62. In this way, bone clamp 58 is attached to femur 54 aligned with respect to the mechanical axis of femur 54, rotation about the mechanical axis end the distance between the femoral head and the knee joint.

Figure 4:
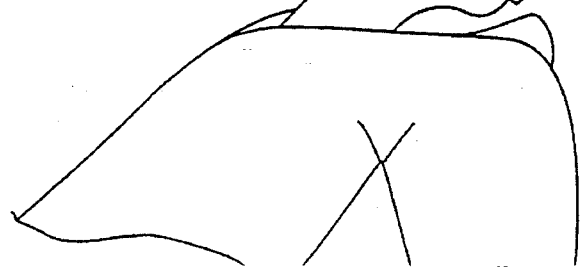
FIG. 4 shows a cutting guide aligned with the bone by the alignment system.

Referring to FIG. 4, the entire alignment jig, consisting of tension reels 32 and 34, support cable 42, tension indicator 44, carriage 56, tension rod 38 and tension cable 86 are removed from connection point 40. Connection point 40 is then removed from femur 54, leaving only the correctly aligned bone clamp 58 attached to femur 54. Advantageously, support arm 30 may be connected to bone clamp 58 to support femur 54 during the course of the surgery.

To perform the cutting of femur 54, saw guide 64 is attached to bone clamp 58. Saw guide 64 provides alignment and stability to a saw blade during the cutting operation.

Many alterations and adaptations may be made to the embodiment described herein. Accordingly, the invention is to be limited only by reference to the appended claims. For example, although the embodiment described is intended for use in alignment of the femur, the same technique could be used to align the tibia during total knee arthroplasty and may be applicable to alignment of various bones for various surgical procedures. Although cables and a tension indicator are used to support the femur and eliminate the effect of weight on the alignment system, offer means for eliminating the weight component, including constant force springs, pneumatic cylinders or other means could achieve the same result. Cables used as pure tension members in this embodiment could be replaced with rigid members connected by universal joints without changing the basic methods used for alignment. Although the preferred embodiment describes a bone clamp which is attached to the distal femur in exact alignment with the mechanical axis, it may be advantageous to attach the bone clamp in any convenient orientation and provide a movable or otherwise adjustable attachment means on the bone clamp which may be aligned with the mechanical axis.

We claim:

1. Method for locating the mechanical axis of a femur in the medial-lateral plane for a supine patient, comprising the steps of:
   (a) applying tension to the femur in the vicinity of the knee joint at a point chosen to be on the mechanical axis;
   (b) allowing the femur to move freely into line with the applied tension; and
   (c) using the axis of the applied tension to indicate the mechanical axis of the femur in the medial-lateral plane.

2. Method for locating the mechanical axis of a femur, comprising the steps of:
   (a) applying a force to the femur to eliminate the moment about the hip joint caused by the weight of the limb;
   (b) applying tension to the femur in the vicinity of the knee joint at a point chosen to be on the mechanical axis;
   (c) allowing the femur to move freely into line with the applied tension; and
   (d) using the axis of the applied tension to indicate the mechanical axis of the femur.

3. Method for locating the mechanical axis of a femur comprising the steps of:
   (a) determining the suspension force required to suspend a femur in a selected location;
   (b) applying tension to the femur in the vicinity of the knee joint at a point chosen to be on the mechanical axis;
   (c) applying the suspension force to the femur to eliminate the effect of weight;
   (d) allowing the femur to move freely into line with the applied tension; and
   (e) using the axis of the applied tension to indicate the mechanical axis of the femur.

4. Apparatus for aligning a surgical instrument to the mechanical axis of the femur, comprising:
   (a) connection means attached to a femur in the vicinity of the knee joint at a point chosen to be on the mechanical axis;
   (b) adjustable vertical suspension means attached to the femur for counteracting the moment about the hip joint created by the weight of the femur;
   (c) vertical tension indicating means attached to the adjustable vertical suspension means for indicating the tension in the vertical suspension means so that the tension in the vertical suspension means can be adjusted to a determined value;
   (d) tension member means attached to the connection means for applying a tension to the femur; and
   (e) a surgical instrument attached to the tension member so that vertical tension required to counteract the moment about the hip joint created by the weight of the femur can be recorded, tension can be applied to the femur with the tension member means and the adjustable vertical suspension means can be adjusted to apply a vertical tension equal to that recorded to align the surgical instrument with the mechanical axis of the femur.

* * * * *

UNITED STATES PATENT AND TRADEMARK OFFICE
CERTIFICATE OF CORRECTION

PATENT NO. : 5,520,694
DATED : May 28, 1996
INVENTOR(S) : Dance et al.

It is certified that error appears in the above-identified patent and that said Letters Patent is hereby corrected as shown below:

Column 1, line 10, "end" should read --and--.

Column 1, line 23, "baring" should read --bearing--.

Column 1, line 40, "were" should read --are--.

Column 1, line 58, "axle" should read --axis--.

Column 1, line 60, "am" should read --are--.

Column 5, line 5, "end" should read --and--.

Column 5, line 9, "86" should read --36--.

Signed and Sealed this

Eighth Day of October, 1996

Attest:

BRUCE LEHMAN

Attesting Officer      Commissioner of Patents and Trademarks